United States Patent [19]

Pratt et al.

[11] Patent Number: 4,499,234
[45] Date of Patent: Feb. 12, 1985

[54] NON-CORROSIVE SILICONE RTV COMPOSITIONS

[75] Inventors: Sandra L. Pratt, Clifton Park; Gary M. Lucas, Scotia, both of N.Y.; Michio Zembayashi, Ohta, Japan

[73] Assignee: General Electric Company, Waterford, N.Y.

[21] Appl. No.: 542,222

[22] Filed: Oct. 14, 1983

[51] Int. Cl.³ .................................................. C08K 3/10
[52] U.S. Cl. .................................... 524/783; 524/785; 524/789; 524/788; 524/860; 524/864; 525/479; 528/18; 528/34; 528/38; 528/901
[58] Field of Search ............ 528/34, 18, 38, 901; 525/479; 524/783, 785, 789, 788, 860, 864

[56] References Cited

U.S. PATENT DOCUMENTS

| 4,395,526 | 7/1983 | White et al. | 528/33 |
| 4,417,042 | 11/1983 | Dziark | 528/18 |
| 4,424,157 | 1/1984 | Chung | 528/33 |

OTHER PUBLICATIONS

Tsai et al., Synthesis of 1,1-diethoxy-2-(trimethylsilyl)-1-sila-2-azacyclopentane, The Journal of Organic Chemistry, vol. 34, No. 11, pp. 3676-3679, Nov. 1969.

Primary Examiner—Melvyn I. Marquis
Attorney, Agent, or Firm—Gary L. Loser

[57] ABSTRACT

Stable, substantially acid-free, one package, moisture curable RTV compositions are provided having a scavenger for chemically combined hydroxy groups of the formula

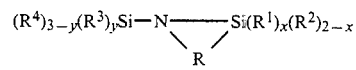

where x equals 1 or 2 and y equals 0 to 3 inclusive. A method for providing the aforesaid moisture curable RTV compositions is also provided. Novel compounds of the formula

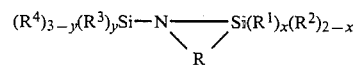

where x equals 1 or 2 and y equals 0 to 2 inclusive are provided as are methods for making such novel compounds.

36 Claims, No Drawings

NON-CORROSIVE SILICONE RTV COMPOSITIONS

BACKGROUND OF THE INVENTION

The present invention relates to one component alkoxy-functional room temperature vulcanizable (RTV) compositions. More particularly, the present invention relates to novel scavengers for chemically combined hydroxy groups usually found in silicone RTV compositions, methods for making such scavenger compounds, and methods for making RTV compositions containing such novel scavenger compounds.

Recently a shelf-stable, fast curing, one component, alkoxy-functional RTV composition was disclosed in the patent of White et al., U.S. Pat. No. 4,395,526, issued July 26, 1983, and assigned to the same assignee as the present invention. Basically White et al. teach that moisture curable, polyalkoxy terminated organopolysiloxane RTV compositions can be made by combining:
(1) a silanol terminated polydiorganosiloxane base polymer,
(2) a crosslinking silane,
(3) an effective amount of certain silane scavengers for chemically combined hydroxy radicals such as methanol, and
(4) an effective amount of a condensation catalyst.

The scavenger of White et al. can be part of the crosslinking silane or a separate compound and must contain a hydrolyzable functional group selected from the group consisting of amido, amino, carbamato, enoxy, imidato, isocyanato, oximato, thioisocyanato and ureido.

Shortly after the pioneering invention of White et al. it was discovered that compounds other than those disclosed by White et al. could be utilized as scavengers for chemically combined hydroxy groups or as integrated scavenger-crosslinkers. Dziark in U.S. patent application Ser. No. 349,695, filed Feb. 17, 1982, now U.S. Pat. No. 4,417,042, discloses silicone scavenger compounds for hydroxy functional groups which are silicone-nitrogen compounds selected from the group consisting of:

(A) a silicone-nitrogen compound having the formula

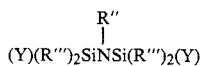

where Y is selected from R''' and R''$_2$N, and (B) a silicone-nitrogen polymer comprising (1) from 3 to 100 mole percent chemically combined structural units selected from the group consisting of units having the formula

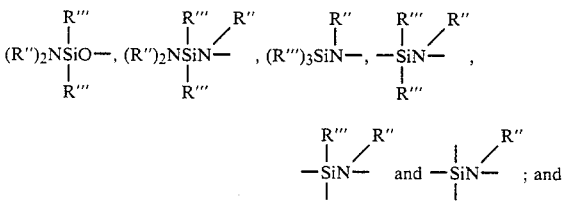

(2) from 0 to 97 mole percent chemically combined structural units represented by the formula $$(R''')_c \text{SiO}_{\frac{4-c}{2}}$$

where the silicone atoms of said silicon-nitrogen polymer are joined to each other by a member selected from an SiOSi linkage and an SiNR''Si linkage, the free valences of said silicon atoms other than those joined to oxygen to form a siloxy unit and nitrogen to form a silazy unit are joined to a member selected from an R''' radical and a (R'')$_2$N radical, and where the ratio of the sum of said R''' radicals and said (R'')$_2$N radicals to the silicon atoms of said silicon-nitrogen polymer has a value of 1.5 to 3, inclusive, and R'' is a member selected from the group consisting of hydrogen, monovalent hydrocarbon radicals and fluoroalkyl radicals, R''' is a member selected from the group consisting of hydrogen, monovalent hydrocarbon radicals and fluoroalkyl radicals, and c is a number equal to 0 to 3 inclusive.

Chung et al. in U.S. patent application, Ser. No. 428,038, filed Sept. 29, 1982, discloses additional silazane scavengers which improve upon those disclosed by Dziark in that they function not only as scavengers for chemically combined hydroxy groups, but as integrated scavenger-crosslinkers.

Additional scavengers for chemically combined hydroxy groups or integrated scavenger-crosslinkers are disclosed in the following U.S. Patent Applications: Lucas, Ser. No. 464,443, filed Feb. 7, 1983, discloses novel acetamide functional silanes and siloxanes; Chung, Ser. No. 338,518, filed Jan. 11, 1982, now U.S. Pat. No. 4,424,157, discloses silanes having cyclic amide functionality; Mitchell, Ser. No. 462,949, filed Feb. 1, 1983, discloses additional amine functional silanes and Swiger et al., Ser. No. 476,000, filed Mar. 17, 1983, discloses additional silane and siloxane scavengers for RTV compositions. All of the foregoing patent applications and the patent of White et al. are assigned to the same assignee as the present invention and are incorporated by reference into the instant disclosure.

One shortcoming of one-component alkoxy-functional RTV compositions such as those described in Dziark, Ser. No. 349,695, now U.S. Pat. No. 4,417,042, and Chung et al., Ser. No. 428,038, is that they tend to be slightly corrosive towards certain metals such as copper and brass. It is believed that this is due to the low molecular weight amino by-products of the scavenging reaction (NH$_3$ in the case of scavengers such as hexamethyldisilazane) causing contact and vapor corrosion of the metal substrate. It should be noted that such corrosion is not extreme as it manifests itself primarily in the form of a dark discoloration.

Accordingly, it is desirable to provide scavengers for chemically combined hydroxy groups whose by-product of the scavenging reaction is innocuous towards the metal substrate.

SUMMARY OF THE INVENTION

It is one object of the present invention to provide novel compounds effective for scavenging chemically combined hydroxy groups which are innocuous toward the metal substrate.

It is another object of the present invention to provide a method for making novel scavenging compounds for use in silicone RTV compositions.

Another object of the present invention is to provide silicone RTV compositions which contain such novel scavenging compounds.

Still another object of the present invention is to provide a method of making silicone RTV compositions which contain the novel scavenging compounds of the present invention.

In accordance with one aspect of the present invention there are provided novel compounds effective as scavengers for chemically combined hydroxy groups having the general formula

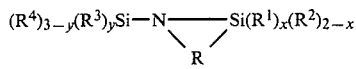

where R is a substituted or unsubstituted organo group having at least two carbon atoms; $R^1$ is a hydrolyzable leaving group selected from the group consisting of alkoxy, amido, amino, carbamato, enoxy, imidato, isocyanato, oximato, thioisocyanato and ureido; $R^2$ and $R^3$ are independently selected $C_{1-13}$ monovalent substituted or unsubstituted hydrocarbon radicals; $R^4$ is a hydrolyzable leaving group selected from the group consisting of alkoxy, amido, amino, carbamato, enoxy, imidato, isocyanato, oximato, thioisocyanato and ureido; x is equal to 1 or 2 and y is equal to 0 to 2 inclusive.

In another aspect of the present invention there is provided a silicone RTV composition comprising:
(1) a polydiorganosiloxane base polymer;
(2) an effective amount of condensation catalyst;
(3) a stabilizing amount of scavenger for hydroxy radicals having the formula

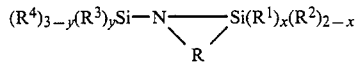

where R is a substituted or unsubstituted organo group having at least two carbon atoms; $R^1$ is a hydrolyzable leaving group selected from the group consisting of alkoxy, amido, amino, carbamato, enoxy, imidato, isocyanato, oximato, thioisocyanato and ureido; $R^2$ and $R^3$ are independently selected $C_{1-13}$ monovalent substituted or unsubstituted hydrocarbon radicals; $R^4$ is a hydrolyzable leaving group selected from the group consisting of alkoxy, amido, amino, carbamato, enoxy, imidato, isocyanato, oximato, thioisocyanato and ureido; x is equal to 1 or 2 and y is equal to 0 to 3; and
(4) optionally, an alkoxy functional crosslinking agent of the formula

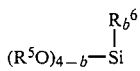

where $R^5$ is a $C_{1-8}$ aliphatic organic radical selected from alkyl radicals, alkylether radicals, alkylester radicals, alkylketone radicals, alkylcyano radicals or a $C_{7-13}$ aralkyl radical; $R^6$ is a $C_{1-13}$ monovalent substituted or unsubstituted hydrocarbon radical; and b equals 0 or 1.

DESCRIPTION OF THE INVENTION

One aspect of the present invention provides novel compounds having utility as scavengers for chemically combined hydroxy groups often found in silicone RTV compositions. Broadly, the novel compounds of the present invention have the formula

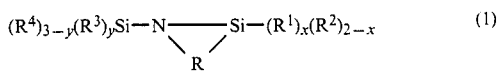

where R is a substituted or unsubstituted organo group having at least two carbon atoms, $R^1$ is a hydrolyzable leaving group selected from the group consisting of alkoxy, amido, amino, carbamato, enoxy, imidato, isocyanato, oximato, thioisocyanato and ureido; $R^2$ and $R^3$ are independently selected $C_{1-13}$ monovalent substituted or unsubstituted hydrocarbon radicals; $R^4$ is a hydrolyzable leaving group selected from the group consisting of alkoxy, amido, amino, carbamato, enoxy, imidato, isocyanato, oximato, thioisocyanato and ureido; x is equal to 1 or 2 and y is equal to 0 to 2 inclusive.

Another aspect of the present invention provides novel silicone RTV compositions comprising:
(1) a polydiorganosiloxane base polymer;
(2) an effective amount of condensation catalyst;
(3) a stabilizing amount of scavenger for hydroxy radicals having the formula

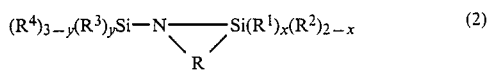

where R is a substituted or unsubstituted organo group having at least two carbon atoms; $R^1$ is a hydrolyzable leaving group selected from the group consisting of alkoxy, amido, amino, carbamato, enoxy, imidato, isocyanato, oximato, thioisocyanato and ureido; $R^2$ and $R^3$ are independently selected $C_{1-13}$ monovalent substituted or unsubstituted hydrocarbon radicals; $R^4$ is a hydrolyzable leaving group selected from the group consisting of alkoxy, amido, amino, carbamato, enoxy, imidato, isocyanato, oximato, thioisocyanato and ureido; x is equal to 1 or 2 and y is equal to 0 to 3 inclusive; and
(4) optionally, an alkoxy-functional crosslinking agent of the formula

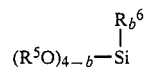

where $R^5$ is a $C_{1-8}$ aliphatic organic radical selected from alkyl radicals, alkylether radicals, alkylester radicals, alkylketone radicals, alkylcyano radicals or a $C_{7-13}$ aralkyl radical; $R^6$ is a $C_{1-13}$ monovalent substituted or unsubstituted hydrocarbon radical and b equals 0 or 1.

Initially it should be noted that the novel compounds of the present invention are defined somewhat more narrowly than are the scavengers of the RTV composition. The reason for such difference is that 1,1-diethoxy-2-(trimethylsilyl)-1-sila-2-azacyclopentane is described in "The Journal of Organic Chemistry", Vol. 34, No. 11, November, 1969, and hence, although such compound is effective as a scavenger for chemically combined hydroxy groups, it is not a novel chemical compound. Accordingly, formula (1) defines y as equal to 0 to 2 inclusive thereby excluding from its scope compounds that do not have at least one hydrolyzable group attached to the silyl-type silicon atom. On the other hand, formula (2) defines y as equal to 0 to 3 inclusive since the previously disclosed 1,1-diethoxy-2-(trimethylsilyl)-1-sila-2-azacyclopentane is also effective as a scavenger for chemically combined hydroxy groups within the scope of the present invention.

Notwithstanding the aforementioned difference, formula (1) and formula (2) are exactly the same. In either case, R can be a substituted or unsubstituted organo group having at least two carbon atoms. Preferably R is a $C_{2-13}$ aliphatic organic radical selected from the group consisting of alkyl, alkenyl, alkynyl, alkylether, alkylester, alkylketone and alkylcyano radicals or a $C_{6-30}$ aromatic organic radical selected from aryl, aralkyl and alkaryl. More preferably, R is a $C_{3-8}$ linear aliphatic organic radical selected from the group consisting of alkyl, alkylether and alkylketone or a $C_{6-18}$ aryl, aralkyl or alkaryl radical.

$R^1$ is a hydrolyzable leaving group selected from the group consisting of alkoxy, amido, amino, carbamato, enoxy, imidato, isocyanato, oximato, thioisocyanato and ureido radicals. Preferably the hydrolyzable group or radical contains from 1 to 13 carbon atoms and more preferably has from 1 to 8 carbon atoms; however, hydrolyzable groups having more than 13 carbon atoms are within the scope of the instant invention. Most preferably $R^1$ is methoxy or ethoxy.

$R^2$ and $R^3$ are independently selected $C_{1-13}$ monovalent substituted or unsubstituted hydrocarbon radicals. Preferably $R^2$ and $R^3$ are lower unsubstituted alkyl radicals such as methyl, ethyl, propyl and butyl. Other suitable radicals include halogenated hydrocarbon radicals, cyanoalkyl radicals, and alkaryl radicals. Most preferably $R^2$ and $R^3$ are either methyl or ethyl.

$R^4$ is defined the same as $R^1$, and preferably $R^1$ and $R^4$ are the same. Accordingly it is most preferable that $R^1$ and $R^4$ are both methoxy or ethoxy.

The most preferred compounds within the scope of formula (1) are:
1,1-dimethoxy-2-(dimethylmethoxysilyl)-2-sila-1-azacyclopentane;
1,1-diethoxy-2-(diethylethoxysilyl)-2-sila-1-azacyclopentane;
1,1-diethoxy-2-(dimethylethoxysilyl)-2-sila-1-azacyclopentane;
1,1-diethoxy-2-(dimethylmethoxysilyl)-1-sila-2-azacyclopentane;
1,ethoxy-1-methoxy-2-(dimethylmethoxysilyl)-1-sila-2-azacyclopentane;
1,1-dimethoxy-2-(methyldimethoxysilyl)-1-sila-2-azacyclopentane.

Other compounds within the scope of formula (1) of the present invention include:
1,1-dimethoxy-2-(dimethylmethoxysilyl)-1-sila-2-aza-3 cyclopentanone and
1,1-dimethoxy-2-(dimethylmethoxysilyl)-1-sila-2-aza-3 cyclohexanone.

Examples of compounds effective as scavengers for chemically combined hydroxy groups within the scope of formula (2), include:
1,1-diethoxy-2-(trimethylsilyl)-1-sila-2-azacyclopentane;
1,1-dimethoxy-2-(trimethylsilyl)-1-sila-2-azacyclopentane;
1,1-diethoxy-2-(trimethylsilyl)-1-sila-2-aza-3-cyclopentanone
1,1-dimethoxy-2-(trimethylsilyl)-1-sila-2-aza-3-cyclopentanone;
1,1-dipropenoxy-2-(trimethylsilyl)-1-sila-2 azacyclopentane;
1,1-bis(dimethylaminoxy)-2-trimethylsilyl-1-sila-2-azacyclopentane;
1,1-diethoxy-2-(dimethylvinylsilyl)-1-sila-2-azacyclopentane;
1,1-diethoxy-2-(dimethylpropylsilyl)-1-sila-2-azacyclopentane;
1,1-diethoxy-2-(triethylsilyl)-1-sila-2-azacyclopentane;
1-methyl-1-ethylamino-2-(trimethylsilyl)-1-sila-2-azacyclopenpentane.

It should be noted that the critical aspect of the compounds of formula (1) and scavengers of formula (2) is that there must be at least one hydrolyzable $R^1$ group. The reason for this is that after the scavenging reaction eliminates substantially all of the chemically combined hydroxy groups in the RTV composition, there will remain in the RTV composition a scavenging reaction product which contains the hydrolyzable $R^1$ group. Thus when the RTV composition is applied to a substrate and curing effected, the residual scavenger will be chemically bound into the cured elastomer as $R^1$ will react with the hydrolyzable end units of the base silicone polymer.

The foregoing is best illustrated by the case wherein the base diorganopolysiloxane is silanol endstopped; i.e. it has the general formula

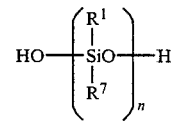

where $R^7$ is a $C_{1-13}$ monovalent substituted or unsubstituted hydrocarbon radical, which is preferably methyl or a mixture of a major amount of methyl and a minor amount of phenyl, cyanoethyl, trifluoropropyl, vinyl and mixtures thereof, and n is an integer having a value of from about 50 to about 2500. It is believed that the scavenger of formula (2) will cleave between the silyl silicon atom and the nitrogen atom as follows:

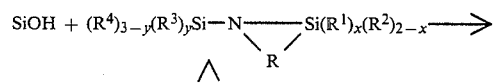

cleavage

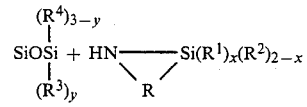

It is also believed that the scavenging reaction product

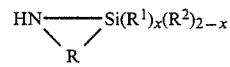

either before or upon exposure of the RTV to the atmosphere to effect curing further scavenges chemically combined hydroxy groups to form a compound of the formula:

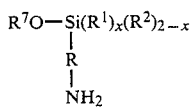

where $R^7$ is hydrogen or a $C_{1-13}$ organic group. Since this has at least two hydrolyzable groups it can act as a coupler or crosslinker and hence be incorporated into the cured elastomer.

Another theory is that the scavenging reaction product

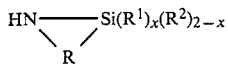

degrades as described above and endcaps silanol polymer much the same as did the $(R^4)_{3-y}(R^3)_y Si$ moiety; i.e. the silanol stopped polymer reacts with the scavenging reaction product to form a

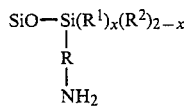

endstopped organopolysiloxane.

In any event, it will be obvious to those skilled in the art that if a silanol endstopped base polymer (diorganopolysiloxane) is employed it is desirable that y equals 0 or 1. Thus when the silanol chainstopper reacts with the scavenger of the formula, for example,

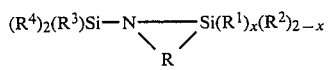

the base polymer will contain at least two terminal hydrolyzable groups which are necessary to effect crosslinking (i.e. curing).

Of course, it is also possible to use as the base polymer a diorganopolysiloxane wherein the silicon atom at each polymer chain end is terminated with at least two hydrolyzable radicals which normally are alkoxy radicals. In such case it is not necessary that the scavenger contain any hydrolyzable $R^4$ groups.

It is not desirable that the base polymer be endstopped with only one hydrolyzable group as in such case coupling rather than crosslinking would occur upon curing. This is not to say that monohydrolyzable (e.g. monoalkoxy) endstopped polymer cannot be included in the base silicone polymer of the present invention. The reader interested in obtaining further information on the use of such monohydrolyzable base polymer is referred to the patent application of G. M. Lucas, Ser. No. 449,105, filed Dec. 13, 1982, and assigned to the same assignee as the present invention, and which is incorporated into the instant disclosure by reference.

The silicone base polymers of the present invention are well known to those skilled in the art and can be made by various procedures. For further information the reader is referred to White et al., U.S. Pat. No. 4,395,526, which is also incorporated by reference into the present disclosure.

Inasmuch as the synthesis of 1,1-diethoxy-2-(trimethylsilyl)-1-sila-2-azacyclopentane is described in "The Journal of Organic Chemistry", Vol. 34, No. 11, November, 1969, and which is hereby incorporated by reference, it is only necessary to describe the method for making the novel compounds of the present invention.

Generally the method for preparing the novel compounds of the present invention is similar to the method for preparing 1,1-diethoxy-2-(trimethylsilyl)-1-sila-2-azacyclopentane. However, instead of reacting 3-aminopropyltriethoxysilane and hexamethyldisilazane in the presence of ammonium sulfate, there is reacted, for example, 3-aminopropyltriethoxysilane and a disilazane having an appropriate number of hydrolyzable radicals, for example $\alpha,\omega$-dimethoxytetramethyldisilazane, in the presence of an acid type catalyst such as ammonium sulfate or the like.

Broadly stated the method for preparing the novel compounds of the present invention is illustrated by the following reaction:

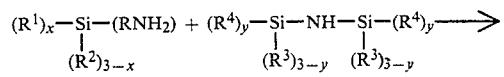

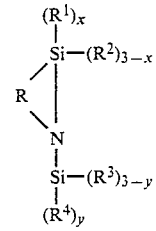

where $R$, $R^1$, $R^2$, $R^3$, $R^4$, x and y are all as previously defined. It will be obvious to the skilled artisan that the silazane need not be a disilazane, but can be any silazane having the appropriate hydrolyzable groups attached to the terminal silicon atoms. Furthermore, it will be obvious that the radicals attached to the silicon atom contained in the ring are determined by the aminosilane reactant, e.g. aminopropyltriethoxysilane, and the radicals attached to the silyl-type silicon atom are determined by the silazane employed, e.g. $\alpha,\omega$-dimethoxytetramethyldisilazane.

Another method for preparing the novel compounds of the present invention is illustrated by the following reaction:

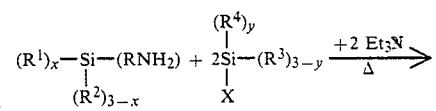

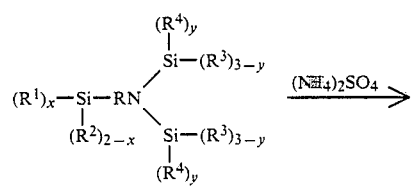

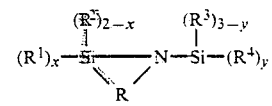

where R, R¹, R², R³, R⁴ are as previously defined, x is equal to 1 to 3 and y is equal to 0 to 3, and X is a halogen, most preferably chlorine.

The catalyst of the RTV composition of the instant invention can be any suitable condensation catalyst. A rather exhaustive listing of suitable condensation catalysts is provided in the disclosure of White et al., U.S. Pat. No. 4,395,526, previously incorporated by reference into the present disclosure. However, it should be noted that tin compounds are the preferred condensation catalysts with dibutyltindi-t-butoxide being the most preferred. Furthermore, it is more desirable to use tin salts of long chain carboxylic acids such as laurate, neodecanoate and the like rather than tin salts of short chain carboxylic acids such as formate, acetate and the like, due to the lower corrosivity of the long chain acid salts. Of course, selecting a suitable condensation catalyst is easily done by the skilled artisan without undue experimentation.

As mentioned hereinabove, if the base polymer is silanol terminated it may be necessary or desirable to include an effective amount of alkoxy function crosslinking agent of the formula

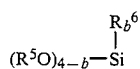
(3)

where $R^5$, $R^6$, and b are as previously defined. It should be understood that in those instances where the scavenger for hydroxy functional groups does not also function as a crosslinking agent, it is necessary that crosslinking agent of formula (3) must be included in the composition, otherwise crosslinking to effect cure of the composition would not be possible. Preferably the crosslinking agent has the formula

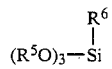

and most preferably is methyltrimethoxysilane.

Various fillers can also be incorporated into the RTV composition of the present invention, for example, titanium dioxide, zirconium silicate, silica aerogel, iron oxide, diatomaceous earth, fumed silica, carbon black, precipitated silica, glass fibers, polyvinylchloride, ground quartz and calcium carbonate. The amount of filler utilized can be varied over wide limits in accordance with the intended use. For example, in some sealant applications the curable composition can be used free of filler whereas in other applications, such as utilizing the curable composition for making binder material, as much as 700 parts or more of filler per 100 parts of organopolysiloxane on a weight basis can be employed. Preferably the filler is present in an amount ranging from 10 to 300 parts per 100 parts organopolysiloxane.

It is also within the scope of the present invention to incorporate small amounts of adhesion promoter, typically 0.1 to 5% by weight, into the RTV composition so as to provide primerless adhesion of the RTV composition to the substrate. Although any suitable adhesion promoter can be employed, it has been found that silane compounds having mixed alkoxy/amino, alkoxy/vinyl, alkoxy/epoxide, alkoxy/cyano, alkoxy/isocyanurate or alkoxy/ester functionality are particularly effective. The preferred adhesive promoters include:

3-(2-aminoethylamino)-propyltrimethoxysilane,
γ-aminopropyltriethoxysilane,
γ-aminopropyltrimethoxysilane,
tris-(trimethoxysilylpropyl) isocyanurate,
γ-glycidoxypropyltrimethoxysilane,
β-(3,4-epoxycyclohexyl)ethyltrimethoxysilane,
vinyltrimethoxysilane,
γ-isocyanatopropyltrimethoxysilane,
β-cyanoethyltrimethoxysilane,
γ-methacryloxypropyltrimethoxysilane and
acetoxypropyltrimethoxysilane.

The most preferred adhesion promoters are tris-(trimethoxysilylpropyl) isocyanurate and 3-(2-aminoethylamino) propyltrimethoxysilane.

Other additives which can be added to the RTV composition of the present invention include sag control agents, plasticizers, cure accelerators and the like.

So that those skilled in the art might be better able to practice the present invention, the following examples are given by way of illustration and not by way of limitation.

EXAMPLES

Example 1

Preparation of 1,1-diethoxy-2-(trimethylsilyl)-1-sila-2-azacyclopentane; CAS Reg. No. 21297-72-3: a three neck round bottom flask fitted with a thermometer, a magnetic stirrer, condenser and nitrogen inlet/outlet was evacuated and filled with nitrogen. The flask was charged with 20 g. (NH₄)₂SO₄, 1.5 moles γ-aminopropyltrimethoxysilane and 1.5 moles hexamethyldisilazane. The reaction mixture was heated to 100° C. for approximately 20 hours. The reaction mixture was then cooled, filtered and distilled to give 1,1-diethoxy-2-(-trimethylsilyl)-1-sila-2-azacyclopentane. The product was identified by its boiling point (literature: b.p.=210° C.) and infared spectrum.

Example 2

Employing the apparatus of Example 1, there was charged to the reaction flask 20 g (NH₄)₂SO₄, 4 moles γ-aminopropyltriethoxysilane and 4 moles α, ω-dimethoxypolydimethylsilazane. The reaction mixture was heated at 130° C. overnight. After cooling the mixture was filtered and the volatiles were stripped off. The remaining pot constituted an equilibrium mixture of 1,1-dialkoxy-2-(dimethylalkoxy)-1-sila-2-azacyclopentane where alkoxy was a mixture of methoxy and ethoxy groups. Identification of the various substituents was made from g.c.-mass spec. data.

Example 3

A suitable mixer equipped with a vacuum line and nitrogen purge was charged with 100 parts by weight methyldimethoxy end-stopped polydimethylsiloxane having a viscosity of about 25,000 cps at 25° C.; 1.4 parts by weight β-cyanoethyltrimethoxysilane, 17.4 parts by weight of fumed silica treated with octamethylcyclotetrasiloxane and 15 parts by weight of dimethylpolysiloxane fluid having a viscosity of about 100 cps at 25° C. as a plasticizer. This mixture was agitated under vacuum (20 mm Hg) at room temperature for 1 hour to give an RTV base. To 100 parts by weight of this base was added 2 parts by weight 1,1-diethoxy-2-(dimethylmethoxysilyl)-1-sila-2-azacyclo pentane; 0.5 parts by weight aminoethylaminopropyltrimethoxysilane, 0.5 parts by weight methyltrimethoxysilane and 0.2 parts by weight dibutyltindi-t-butoxide using a Semco ® catalyzer/mixer. Following mixing, a complete property profile was obtained as set forth in Table I.

TABLE I

| Property | |
|---|---|
| Sp. Gravity | 1.042 |
| App. Rate, g/min. | 293 |
| Flow, in. | 0.10 |
| Tack Free Time, min. | 10 |
| Durometer, Shore A* | 30 |
| Tensile, psi | 288 |
| Elongation, %* | 402 |
| 50% Modulus | 63 |
| Accelerated Shelf Age** 48 hr/100° C. | |
| Shore A | 27 |
| Tensile, psi | 287 |
| Elongation, % | 462 |
| Tack Free Time, min. | 60 |
| Heat Resistance 7 da./200° C. | |
| Shore A | 29 |
| Tensile, psi | 353 |
| Elongation, % | 453 |
| Corrosion | |
| Vapor | Pass |
| Contact | Pass |
| Peel Adhesion** ppi/% C.F. | |
| Glass | 52/100 |
| Stainless | 70/100 |
| Fiberglass | 63/100 |
| Epoxy-Glass | 56/100 |
| Mill Fin. Alum. | 73/100 |
| Copper | 57/100 |
| Cold Rolled Steel | 71/100 |
| Polycarbonate | 45/30 |

*3 day cure at 50% R. H. and Room Temperature
**7 day cure at 50% R. H. and Room Temperature Example 4

Example 3 was repeated but 0.5 parts by weight per 100 parts by weight base of tris (trimethyoxysilylpropyl)-isocyanurate was used as co-adhesion promoter instead of aminoethylaminopropyltrimethoxysilane. Also the condensation catalyst employed was 0.2 parts by weight dibutyltindiacetate rather than dibutyltindi-t-butoxide. Again, a complete property profile was obtained as set forth in Table II.

TABLE II

| Property | |
|---|---|
| Sp. Gravity | 1.042 |
| App. Rate, g/min. | 324 |
| Flow, in. | 0.05 |
| Tack Free Time, min. | 10 |
| Durometer, Shore A* | 25 |
| Tensile, psi | 368 |
| Elongation, %* | 425 |
| 50% Modulus | 76 |
| Accelerated Shelf Age** 48 hr/100° C. | |
| Shore A | 28 |
| Tensile, psi | 213 |
| Elongation, % | 401 |
| Tack Free Time, min. | 60 |
| Heat Resistance 7 da./200° C. | |
| Shore A | 29 |
| Tensile, psi | 321 |
| Elongation, % | 414 |
| Corrosion | |
| Vapor | Pass |
| Contact | Pass |
| Peel Adhesion** ppi/% C.F. | |

TABLE II-continued

| | |
|---|---|
| Glass | 56/100 |
| Stainless | 25/25 |
| Fiberglass | 51/100 |
| Epoxy-Glass | 44/90 |
| Mill Fin. Alum. | 53/100 |
| Copper | 48/100 |
| Cold Rolled Steel | 54/90 |
| Polycarbonate | 0/0 |

*3 day cure at 50% R. H. and Room Temperature
**7 day cure at 50% R. H. and Room Temperature Example 5

Example 3 was again repeated, but 0.25 parts by weight per 100 parts by weight base of dibutyltindilaurate was used as the catalyst. The results of the property profile obtained are set forth in Table III.

TABLE III

| Property | |
|---|---|
| Sp. Gravity | 1.054 |
| App. Rate, g/min. | 150 |
| Flow, in. | 0.05 |
| Tack Free Time, min. | 10 |
| Durometer, Shore A* | 35 |
| Tensile, psi | 348 |
| Elongation, %* | 413 |
| 50% Modulus | 86 |
| Accelerated Shelf Age** 48 hr/100° C. | |
| Shore A | 30 |
| Tensile, psi | 260 |
| Elongation, % | 442 |
| Tack Free Time, min. | 20 |
| Corrosion | |
| Vapor | Pass |
| Contact | Pass |
| Peel Adhesion** ppi/% C.F. | |
| Glass | 80/100 |
| Stainless | 105/100 |
| Mill Fin. Alum. | 95/100 |
| Copper | 7/0 |
| Cold Rolled Steel | 54/40 |

*3 day cure at 50% R. H. and Room Temperature
**7 day cure at 50% R. H. and Room Temperature Example 6

A suitable mixer equipped with a vacuum line and nitrogen purge was charged with 100 parts by weight methyldimethoxy endstopped polydimethylsiloxane having a viscosity of 12000 cps at 25° C., 1.4 parts by weight cyanoethyltrimethoxysilane, 20 parts by weight octamethylcyclotetrasiloxane treated fumed silica, and 15 parts by weight of a dimethylpolysiloxane fluid having a viscosity of 100 cps at 25° C. as a plasticizer. This mixture was agitated under vacuum (20 mm Hg) at room temperature for 1 hour to give an RTV base. To 100 parts by weight of this base was added 2 parts by weight 1,1-diethoxy-2-(trimethylsilyl)-1-sila-2-azacyclopentane; 0.5 parts by weight aminoethylaminopropyltrimethoxysilane; 0.5 parts by weight methyltrimethoxysilane and 0.2 parts by weight dibutyltindi-t-butoxide using a 15 minute mix at room temperature in a Semco ® catalyzer/mixer. A physical property profile was done at room temperature after heat aging for 48 hours at 100° C. The results are set forth in Table IV.

TABLE IV

| Property | |
|---|---|

TABLE IV-continued

| | |
|---|---|
| Tack Free Time, min. | 10 |
| Durometer, Shore A* | 28 |
| Tensile, psi | 344 |
| Elongation, %* | 485 |
| 50% Modulus | 71 |
| Accelerated Shelf Age** 48 hr/100° C. | |
| Shore A | 26 |
| Tensile, psi | 315 |
| Elongation, % | 487 |
| Tack Free Time, min. | 10 |
| Corrosion | |
| Vapor | Pass |
| Contact | Pass |

*3 day cure at 50% R. H. and Room Temperature
**7 day cure at 50% R. H. and Room Temperature

Example 7

To establish that RTV compositions prepared in accordance with the present invention are less corrosive than prior art compositions, a sample was prepared according to Example 3, but the 1,1-diethoxy-2-(dimethylmethoxysilyl)-1-sila-2-azacyclopentane was replaced with the hexamethyldisilazane scavenger described in Dziark, U.S. patent application, Ser. No. 349,695, filed Feb. 17, 1982. The corrosiveness of the composition was evaluated for vapor and contact corrosion as per Mil-A-46146 (U.S. Department of Defense Military Specification) as follows:

(a) Vapor Corrosion Test

Two panels (4 inches by 1 inch) were prepared from a copper alloy sheet by cleaning with a number 400 emery cloth, rinsing with acetone and blotting dry. 15 grams of the hexamethyldisilazane-containing RTV composition were extruded into an 8 ounce glass bottle equipped with a polytetrafluoroethylene cup. Five to ten milliliters of distilled water were poured over the RTV composition and one brass panel was hung above the silicone and water mix. The bottle was then tightly capped. The second panel was hung in a control bottle containing five to ten milliliters of distilled water only. The test and control bottles were maintained at 100°±4° F. for 7 days. At the end of this period the panels were removed from the bottles and visually inspected for corrosion and/or discoloration. The control panel remained unchanged whereas the test panel was severely discolored, thus failing the vapor corrosion test.

(b) Contact Corrosion Test

Two 1.5 inch lengths of AWG size copper wire were prepared by removing all insulation and then cleaning with acetone. One wire specimen was encapsulated by placing it into a mold 1 inch by 2 inches by ¼ inch and filling the mold with the same RTV composition used in the vapor corrosion test. The composition was cured at 77° F. and 50% relative humidity for 7 days. The thus encapsulated specimen and the second unpotted control wire specimen were placed in a 95% relative humidity, 120° F. environment for 28 days. At the end of the test period the wires were visually inspected for corrosion and/or discoloration. The unpotted wire was unchanged whereas the potted wire exhibited severe dark discoloration, thus failing the contact corrosion test.

Example 8

Vapor and contact corrosion tests as described in Example 7 were performed on an acetoxy type sealant (within the scope of the claims of U.S. Pat. Nos. 3,296,161, 3,296,195 and 3,382,205) sold by General Electric Company under the trademark SCS-1201 with the following results:

| Corrosion Test | Result |
|---|---|
| Vapor | Failed |
| Contact | Failed. |

As can be seen from Tables I through IV, unlike prior art RTV compositions, the RTV compositions of the present invention are less corrosive.

I claim:

1. A stable, one package, substantially anhydrous and substantially acid-free, room temperature vulcanizable organopolysiloxane composition stable under ambient conditions in the substantial absence of moisture over an extended period of time and convertible to a tack free elastomer comprising:
(a) a polydiorganosiloxane base polymer,
(b) an effective amount of condensation catalyst, and
(c) a stabilizing amount of scavenger for hydroxy functional groups having the formula

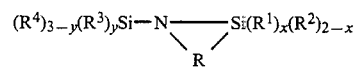

$$(R^4)_{3-y}(R^3)_y Si-N \underset{R}{\diagdown \diagup} Si(R^1)_x(R^2)_{2-x}$$

where R is a substituted or unsubstituted organo group having at least two carbon atoms; $R^1$ is a hydrolyzable leaving group selected from the group consisting of alkoxy, amido, amino, carbamato, enoxy, imidato, isocyanato, oximato, thioisocyanato, and ureido; $R^2$ and $R^3$ are independently selected $C_{1-13}$ monovalent substituted or unsubstituted hydrocarbon radicals; $R^4$ is a hydrolyzable leaving group selected from the group consisting of alkoxy, amido, amino, carbamato, enoxy, imidato, isocyanato, oximato, thioisocyanato and ureido; x is equal to 1 or 2 and y is equal to 0 to 3 inclusive.

2. The composition of claim 1 wherein R is a $C_{2-13}$ aliphatic organic radical selected from the group consisting of alkyl, alkenyl, alkynyl, alkylether, alkylester, alkylketone and alkylcyano or a $C_{6-30}$ aromatic organic radical selected from aryl, aralkyl and alkaryl.

3. The composition of claim 1 wherein R is a $C_{3-8}$ linear aliphatic organic radical selected from the group consisting of alkyl, alkylether and alkylketone or a $C_{6-18}$ aromatic organic radical selected from aryl, aralkyl and alkaryl.

4. The composition of claim 1 wherein $R^1$ has from 1 to 13 carbon atoms.

5. The composition of claim 1 wherein $R^1$ has from 1 to 8 carbon atoms.

6. The composition of claim 1 wherein $R^2$ and $R^3$ have from 1 to about 4 carbon atoms, respectively.

7. The composition of claim 1 wherein $R^2$ and $R^3$ are independently selected from methyl and ethyl.

8. The composition of claim 1 wherein $R^4$ has from 1 to 13 carbon atoms.

9. The composition of claim 1 wherein $R^4$ has from 1 to 8 carbon atoms.

10. The composition of claim 1 wherein the scavenger for hydroxy functional groups is selected from the group consisting of:
1,1-dimethoxy-2-(dimethylmethoxysilyl)-2-sila-1-azacyclopentane,
1,1-diethoxy-2-(diethylethoxysilyl)-2-sila-1-azacyclopentane and
1,1-diethoxy-2-(dimethylethoxysilyl)-2-sila-1-azacyclopentane.

11. The composition of claim 1 wherein the polydiorganosiloxane base polymer is silanol terminated.

12. The composition of claim 11 wherein the scavenger for hydroxy functional groups has the formula

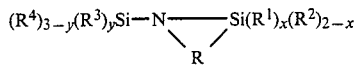

where R is a substituted or unsubstituted organo group having at least two carbon atoms, $R^1$ is a hydrolyzable leaving group selected from the group consisting of alkoxy, amido, amino, carbamato, enoxy, imidato, isocyanato, oximato, thioisocyanato and ureido, $R^2$ and $R^3$ are independently selected $C_{1-13}$ monovalent substituted or unsubstituted hydrocarbon radicals, $R^4$ is a hydrolyzable leaving group selected from the group consisting of alkoxy, amido, amino, carbamato, enoxy, imidato, isocyanato, oximato, thioisocyanato and ureido, x is equal to 1 or 2 and y is equal to 0 or 1.

13. The composition of claim 11 further comprising an effective amount of crosslinking silane of the formula

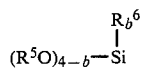

where $R^5$ is a $C_{1-8}$ aliphatic organic radical selected from the group consisting of alkyl, alkylether, alkyester, alkylketone and alkylcyano radicals or a $C_{7-13}$ aralkyl radical, $R^6$ is a $C_{1-13}$ monovalent substituted or unsubstituted hydrocarbon radical and b equals 0 or 1.

14. The composition of claim 11 wherein the scavenger for hydroxy functional groups has the formula

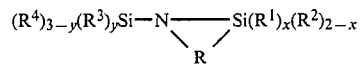

where R is a substituted or unsubstituted organo group having at least two carbon atoms, $R^1$ is a hydrolyzable leaving group selected from the group consisting of alkoxy, amido, amino, carbamato, enoxy, imidato, isocyanato, oximato, thioisocyanato and ureido radicals, $R^2$ and $R^3$ are independently selected $C_{1-13}$ monovalent substituted or unsubstituted hydrocarbon radicals, $R^4$ is a hydrolyzable leaving group selected from the group consisting of alkoxy, amido, amino, carbamato, enoxy, imidato, isocyanato, oximato, thioisocyanato and ureido, x is equal to 1 or 2 and y is equal to 2 or 3; further comprising an effective amount of crosslinking silane of the formula

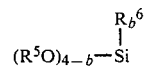

where $R^5$ is a $C_{1-8}$ aliphatic organic radical selected from the group consisting of alkyl, alkylether, alkyester, alkylketone, and alkylcyano radicals or a $C_{7-13}$ aralkyl radical, $R^6$ is a $C_{1-13}$ monovalent substituted or unsubstituted hydrocarbon radical and b equals 0 or 1.

15. The composition of claim 1 wherein the polydiorganosiloxane base polymer is terminated at each chain end with at least two hydrolyzable groups.

16. The composition of claim 15 wherein the hydrolyzable groups are alkoxy groups.

17. The composition of claim 1 wherein the condensation catalyst is a tin compound.

18. The composition of claim 17 wherein the tin condensation catalyst is dibutyltindi-t-butoxide.

19. The composition of claim 1 further comprising a filler selected from the group consisting of titanium dioxide, zirconium silicate, silica aerogel, iron oxide, diatomaceous earth, fumed silica, carbon black, precipitated silica, glass fibers, polyvinylchloride, ground quartz and calcium carbonate.

20. The composition of claim 1 further comprising an adhesion promoter.

21. The composition of claim 20 wherein the adhesion promoter is selected from the group consisting of:
3-(2-aminoethyl)aminopropyltrimethoxysilane,
γ-aminopropyltriethoxysilane,
γ-aminopropyltrimethoxysilane,
tris-(trimethoxysilylpropyl)isocyanurate,
γ-glycidoxypropyltrimethoxysilane,
β-(3,4-epoxycyclohexyl)ethyltrimethoxysilane,
vinyltrimethoxysilane,
γ-isocyanatopropyltrimethoxysilane,
β-cyanoethyltrimethoxysilane,
γ-methacryloxypropyltrimethoxysilane and
acetoxypropyltrimethoxysilane.

22. The composition of claim 1 further comprising a sag control agent.

23. The composition of claim 1 further comprising a plasticizer.

24. The composition of claim 1 further comprising a cure accelerator.

25. A method for making a stable, one package, substantially anhydrous and substantially acid-free, room temperature vulcanizable organopolysiloxane composition curable to the solid elastomeric state, which method comprises agitating under substantially anhydrous conditions at a temperature in the range of from 0° C. to 180° C., a room temperature vulcanizable material comprising a mixture of:
(a) 100 parts of a polydiorganosiloxane base polymer,
(b) an effective amount of condensation catalyst, and
(c) a stabilizing amount of scavenger for hydroxy functional groups having the formula

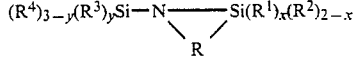

where R is a substituted or unsubstituted organo group having at least two carbon atoms, $R^1$ is a hydrolyzable leaving group selected from the group consisting of alkoxy, amido, amino, carbamato, enoxy, imidato, isocyanato, oximato, thioisocyanato and ureido; $R^2$ and $R^3$ are independently selected $C_{1-13}$ monovalent substituted or unsubstituted hydrocarbon radicals, $R^4$ is a hydrolyzable leaving group selected from the group consisting of alkoxy, amido, amino, carbamato, enoxy, imidato, isocyanato, oximato, thioisocyanato and ureido, x is equal to 1 or 2 and y is equal to 0 to 3 inclusive.

26. The method of claim 25 wherein R is a $C_{2-13}$ aliphatic organic radical selected from the group consisting of alkyl, alkenyl, alkynyl, alkylether, alkylester, alkylketone and alkylcyano or a $C_{6-30}$ aromatic organic radical selected from aryl, aralkyl, and alkaryl.

27. The method of claim 25 wherein $R^1$ has from 1 to 13 carbon atoms.

28. The method of claim 25 wherein $R^2$ and $R^3$ have from 1 to about 4 carbon atoms, respectively.

29. The method of claim 25 wherein $R^4$ has from 1 to 13 carbon atoms.

30. The method of claim 25 wherein the scavenger for hydroxy functional groups is selected from the group consisting of:
1,1-dimethoxy-2-(dimethylmethoxysilyl)-2-sila-1-azacyclopentane,
1,1-diethoxy-2-(diethylethoxysilyl)-2-sila-1-azacyclopentane and
1,1-diethoxy-2-(dimethylethoxysilyl)-2-sila-1-azacyclopentane.

31. The method of claim 25 further comprising adding and agitating under substantially anhydrous conditions at a temperature in the range of from 0° C. to 180° C., an effective amount of crosslinking silane of the formula

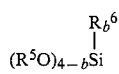

where $R^5$ is a $C_{1-8}$ aliphatic organic radical selected from the group consisting of alkyl, alkylether, alkylester, alkylketone and alkylcyano radicals or a $C_{7-13}$ aralkyl radical; $R^6$ is a $C_{1-13}$ monovalent substituted or unsubstituted hydrocarbon radical and b equals 0 or 1.

32. The method of claim 25 further comprising adding and agitating under substantially anhydrous conditions at a temperature in the range of from 0° C. to 180° C., a filler selected from the group consisting of titanium dioxide, zirconium silicate, silica aerogel, iron oxide, diatomaceous earth, fumed silica, carbon black, precipitated silica, glass fibers, polyvinylchloride, ground quartz and calcium carbonate.

33. The method of claim 25 further comprising adding and agitating under substantially anhydrous conditions at a temperature in the range of from 0° C. to 180° C., an adhesion promoter selected from the group consisting of:
3-(2-aminoethyl)aminopropyltrimethoxysilane,
γ-aminopropyltriethoxysilane,
γ-aminopropyltrimethoxysilane,
tris-(trimethoxysilylpropyl)isocyanurate,
γ-glycidoxypropyltrimethoxysilane,
β-(3,4-epoxycyclohexyl)ethyltrimethoxysilane,
vinyltrimethoxysilane,
γ-isocyanatopropyltrimethoxysilane,
β-cyanoethyltrimethoxysilane,
γ-methacryloxypropyltrimethoxysilane and
acetoxypropyltrimethoxysilane.

34. The method of claim 25 further comprising adding and agitating under substantially anhydrous conditions at a temperature in the range of from 0° C. to 180° C., a sag control agent.

35. The method of claim 25 further comprising adding and agitating under substantially anhydrous conditions at a temperature in the range of from 0° C. to 180° C., a plasticizer.

36. The method of claim 25 further comprising adding and agitating under substantially anhydrous conditions at a temperature in the range of from 0° C. to 180° C., a cure accelerator.

* * * * *